United States Patent
Wang et al.

(10) Patent No.: US 8,603,803 B2
(45) Date of Patent: *Dec. 10, 2013

(54) SOLID PHASE ELECTROCHEMICAL SYNTHESIS WITH CONTROLLED PRODUCT CLEAVAGE

(75) Inventors: Wei Wang, San Jose, CA (US); Yuan Gao, Mountain View, CA (US)

(73) Assignee: Intel Corporation, Santa Clara, CA (US)

( * ) Notice: Subject to any disclaimer, the term of this patent is extended or adjusted under 35 U.S.C. 154(b) by 716 days.

This patent is subject to a terminal disclaimer.

(21) Appl. No.: 12/315,895

(22) Filed: Dec. 8, 2008

(65) Prior Publication Data
US 2009/0093381 A1    Apr. 9, 2009

(51) Int. Cl.
| C12M 1/00 | (2006.01) |
| C12M 1/34 | (2006.01) |
| C12Q 1/68 | (2006.01) |
| G01N 27/00 | (2006.01) |
| C07H 19/00 | (2006.01) |
| C07H 21/00 | (2006.01) |

(52) U.S. Cl.
USPC ... 435/283.1; 435/6.1; 435/287.2; 422/82.01; 536/22.1; 536/25.3; 205/122; 205/334; 205/414; 530/300; 977/701; 977/704; 977/705

(58) Field of Classification Search
USPC .................. 435/6.1, 283.1, 287.2; 422/82.01; 530/300; 536/22.1, 23.1, 25.3; 205/122, 334, 414; 977/701, 704, 705
See application file for complete search history.

(56) References Cited

U.S. PATENT DOCUMENTS

| 5,143,854 | A | 9/1992 | Pirrung et al. |
| 5,352,574 | A | 10/1994 | Guiseppi-Elie |
| 5,405,783 | A | 4/1995 | Pirrung et al. |
| 5,552,270 | A | 9/1996 | Khrapko et al. |
| 5,653,930 | A | 8/1997 | Noda et al. |
| 5,653,939 | A | 8/1997 | Hollis et al. |
| 5,667,667 | A | 9/1997 | Southern |
| 5,766,934 | A | 6/1998 | Guiseppi-Elie |
| 5,837,859 | A | 11/1998 | Teoule et al. |
| 5,874,219 | A | 2/1999 | Rava et al. |
| 6,093,302 | A | 7/2000 | Montgomery |
| 6,121,048 | A | 9/2000 | Zaffaroni et al. |
| 6,239,273 | B1 | 5/2001 | Pease et al. |
| 6,251,595 | B1 | 6/2001 | Gordon et al. |
| 6,258,606 | B1 | 7/2001 | Kovacs |
| 6,280,595 | B1 | 8/2001 | Montgomery |
| 6,309,833 | B1 | 10/2001 | Edman et al. |
| 6,379,895 | B1 | 4/2002 | Fodor et al. |
| 6,406,844 | B1 | 6/2002 | Pirrung et al. |
| 6,416,952 | B1 | 7/2002 | Pirrung et al. |
| 6,444,111 | B1 | 9/2002 | Montgomery |
| 6,456,942 | B1 | 9/2002 | Anderson |
| 6,506,558 | B1 | 1/2003 | Fodor et al. |
| 6,515,039 | B1 | 2/2003 | Ulbricht et al. |
| 6,518,022 | B1 | 2/2003 | Sosnowski et al. |
| 6,566,495 | B1 | 5/2003 | Fodor et al. |
| 6,569,382 | B1 | 5/2003 | Edman et al. |
| 6,602,400 | B1 * | 8/2003 | Choong et al. ..................... 506/9 |
| 6,630,308 | B2 | 10/2003 | Stryer et al. |
| 6,682,936 | B2 | 1/2004 | Kovacs |
| 6,770,436 | B1 | 8/2004 | Beecher et al. |
| 6,819,843 | B1 | 11/2004 | Braun et al. |
| 6,867,048 | B2 | 3/2005 | Kovacs |
| 6,919,211 | B1 | 7/2005 | Fodor et al. |
| 7,615,343 | B2 * | 11/2009 | Franzen et al. .................... 435/6 |
| 7,622,295 | B2 | 11/2009 | Cabezas |
| 7,776,269 | B2 | 8/2010 | Snow et al. |
| 7,923,237 | B2 * | 4/2011 | Castro et al. ............... 435/283.1 |
| 2004/0058438 | A1 | 3/2004 | Fujii et al. |
| 2005/0014146 | A1 | 1/2005 | Manaresi et al. |
| 2005/0181409 | A1 | 8/2005 | Park et al. |
| 2006/0105373 | A1 * | 5/2006 | Pourmand et al. ................. 435/6 |
| 2006/0263897 | A1 | 11/2006 | Stapert et al. |
| 2006/0275927 | A1 | 12/2006 | Dubin et al. |
| 2007/0065877 | A1 * | 3/2007 | Maurer .......................... 435/7.1 |
| 2007/0122842 | A1 | 5/2007 | Rajasekaran et al. |
| 2007/0154946 | A1 | 7/2007 | Rajasekaran et al. |
| 2007/0292855 | A1 | 12/2007 | Dubin et al. |
| 2008/0108149 | A1 | 5/2008 | Sundararajan et al. |
| 2008/0157786 | A1 | 7/2008 | Holt et al. |
| 2008/0160635 | A1 | 7/2008 | Castro et al. |
| 2008/0161202 | A1 | 7/2008 | Cabezas et al. |
| 2009/0000957 | A1 | 1/2009 | Dubin et al. |
| 2010/0240544 | A1 | 9/2010 | Liu et al. |
| 2010/0240555 | A1 | 9/2010 | Sundararajan et al. |
| 2010/0248975 | A1 | 9/2010 | Tiwari et al. |

OTHER PUBLICATIONS

U.S. Appl. No. 11/646,615, "Method and Apparatus for Match Quality Analysis of Analyte Binding", filed Dec. 28, 2006.
Guiducci, C. et al., "A Biosensor for Direct Detection of DNA Sequences Based on Capacitance Measurements", ESSDERC, 2002, pp. 279-282.
Guiducci, C. et al., "DNA Detection by Integrable Electronics", dated Jul. 9, 2003, Biosensors and Bioelectronics 19, 2004, pp. 781-787.
Maurer, Karl et al., "Electrochemically Generated Acid and Its Containment to 100 Micron Reaction Areas for the Production of DNA Microarrays", dated Dec. 2006, PLoS One 1(1): e34. doi:10.1371/journal.pone.0000034, pp. 1-7.

(Continued)

Primary Examiner — Narayan Bhat

(57) ABSTRACT

Methods for electrochemically synthesizing polymers are provided in which a cleavable linker is coupled to the surface of at least one electrode of an array of electrodes on a substrate and a polymer coupled to the cleavable linker is synthesized through a series of monomer addition cycles. Polymers that are synthesized include nucleic acids and peptides. Cleavable linkers include linkers that can be cleaved under conditions such as reducing, oxidizing, acidic, and or basic conditions. Additionally, provided are devices that comprise an array of individually addressable electrodes having surface-attached cleavable linker molecules.

29 Claims, 10 Drawing Sheets

(56) References Cited

OTHER PUBLICATIONS

Pouthas, F. et al., "Spatially Resolved Electronic Detection of Biopolymers", dated Sep. 21, 2004, Physical Review E 70, 031906, 2004, pp. 031906-1-031906-8.

Goncalves D. et al., "Label-free Electronic Detection of Biomolecules Using A-Si:H Field-effect Devices", dated Apr. 4, 2006, Journal of Non-Crystalline Solids 352, 2006, pp. 2007-2010.

Egeland, Ryan D., "An Electrochemical Redox Couple Activitated by Microelectrodes for Confined Chemical Patterning of Surfaces", Analytical Chemistry, vol. 74, No. 7, Apr. 1, 2002, pp. 1590-1596.

Hodneland, C. D. et al., "Bimolecular Surfaces that Release Ligands under Electrochemical Control," J. Am. Chemical Society, vol. 122, No. 17, 2000, pp. 4235-4236.

Pon, Richard T. et al., "Linker Phosphoramidite Reagents for Oligonucleotide Synthesis on Underivatized Solid-Phase Supports, Tetrahedron Letters", 42, 2001, pp. 8943-8946.

Overview of Peptide Synthesis, AnaSpec, Peptide Notes, retrieved on Apr. 17, 2009, 11 Pages. http://www.anaspec.com/resources/peptide.asp.

Olejnik, Jerzy et al., "Photocleavable peptide-DNA conjugates: synthesis and applications to DNA analysis using MALDI-MS", Nucleic Acids Research, vol. 27 No. 23, 1999, pp. 4626-4631.

Patek, M. et al. "Safety-Catch and Multiply Cleavable Linkers in Solid-Phase Synthesis," Biopolymers (Peptide Science), vol. 47, 1998, pp. 353-363.

U.S. Appl. No. 11/478,335, "Three-Dimensional Integrated Circuit for Analyte Detection", filed Jun. 30, 2006.

U.S. Appl. No. 12/059,833, "Optical Detection for Electronic Microarrays", filed Mar. 31, 2008.

U.S. Appl. No. 12/217,087, "Density Modification in Arrays of Surface-Attached Nucleic Acid Molecules", filed Jun. 30, 2008.

U.S. Appl. No. 12/217,097, "Polymer Co-Location in Surface-Attached Biopolymers and Arrays of Biopolymers", filed Jun. 30, 2008.

Pellois et al., "Individually Addressable Parallel Peptide Synthesis on Microchips", Research Article, Nature biotechnology, vol. 20, Sep. 2002, pp. 922-926.

Willson et al., "Approaches to the Design of Radiation-Sensitive Polymeric Imaging Systems with Improved Sensitivity and Resolution", Journal of Electrochemical Society, Solid-State Science and Technology, vol. 133, Issue 1, Jan. 1986, pp. 181-187.

Hamamatsu, "Technical Information SD-37: Characteristics and Use of Charge Amplifier", Solid State Division, Oct. 2001, pp. 1-10.

Reynolds et al., "Homogeneous, Nanoparticle-Based Quantitative Colorimetric Detection of Oligonucleotides", Journal of the American Chemical Society, vol. 122, Issue 15. Apr. 4, 2000, pp. 3795-3796.

Steemers et al., "Screening unlabeled DNA targets with randomly ordered fiber-optic gene arrays". Research Articles, Nature Biotechnology, vol. 18, Jan. 2000, pp. 91-94.

Fedurco et al., "BTA, a novel reagent for DNA attachment on glass and efficient generation of solid-phase amplified DNA colonies", Nucleic Acids Research, vol. 34, No. 3, e22, Feb. 9, 2006, pp. 1-13.

Shumaker-Parry et al., "Parallel, Quantitative Measurement of Protein Binding to a 120-Element Double-Stranded DNA Array in Real Time Using Surface Plasmon Resonance Microscopy", Analytical Chemistry, vol. 76, No. 7, Apr. 1, 2004, pp. 2071-2082.

Benters et al., "DNA microarrays with PAMAM dendritic linker systems", Nucleic Acids Research, vol. 30, No. 2, 2002, pp. 1-7.

Immoos et al., "DNA-PEG-DNA Triblock Macromolecules for Reagentless DNA Detection", Journal of the American Chemical Society, vol. 126, No. 35, Aug. 17, 2004. pp. 10814-10815.

Brockman et al., "A Multistep Chemical Modification Procedure to Create DNA Arrays on Gold Surfaces for the Study of Protein-DNA Interactions with Surface Plasmon Resonance Imaging", Journal of the American Chemical Society, vol. 121, No. 35, Aug. 19, 1999, pp. 8044-8051.

\* cited by examiner

ACID CLEAVABLE LINKER

BASE CLEAVABLE LINKER

REDUCTION CLEAVABLE LINKER

OXIDATION CLEAVABLE LINKER

SOLID PHASE ELECTROCHEMICAL SYNTHESIS WITH CONTROLLED PRODUCT CLEAVAGE

CROSS REFERENCE TO RELATED APPLICATIONS

The present application is related to U.S. patent application Ser. No. 11/646,602, entitled "Method and Apparatus for Combined Electrochemical Synthesis and Detection of Analytes," filed Dec. 28, 2006, now pending, U.S. patent application Ser. No. 11/646,615, entitled "Method and Apparatus for Match Quality Analysis of Analyte Binding," filed Dec. 28, 2006, now pending, U.S. patent application Ser. No. 11/646,600, entitled "Quality Control Methods for the Manufacture of Polymer Arrays" filed Dec. 28, 2006, now pending, U.S. patent application Ser. No. 12/059,833, entitled "Optical Detection for Electronic Microarrays," filed Mar. 31, 2008, now pending, and U.S. patent application Ser. No. 12/217,097, entitled "Density Modification in Arrays of Surface-Attached Nucleic Acid Molecules," filed Jun. 30, 2008, now pending, the disclosures of which are considered part of and are incorporated by reference in the disclosure of this application.

BACKGROUND OF THE INVENTION

1. Field of the Invention

The embodiments of the present invention relate generally to methods for monitoring the synthesis of polymers on an electrode surface, to polymers incorporating cleavable linkers, and to electrochemical polymer synthesis and detection devices.

2. Background Information

Microarrays of nucleic acids, peptides, proteins, and oligosaccharides continue to gain importance as powerful tools for research and diagnostic applications in the biomedical sciences. Nucleic acid microarrays, for example, can be used to monitor gene expression and genetic mutations in a massively parallel manner. Proteinaceous microarrays provide the ability to characterize the molecular progression of disease, research cellular pathways, and perform high throughput screening in drug discovery applications. The ability to collect large volumes of information is an integral part of biomarker discovery and personalization of medical treatments. Further, other applications in bioscience, such as for example, the analysis of the proteomic content of an organism, disease detection, pathogen detection, environmental protection, food safety, and biodefense are capable of benefiting from tools that allow rapid multiplexed interrogation of analyte samples.

Genetic information in living organisms is contained in the form of very long nucleic acid molecules such as deoxyribonucleic acid (DNA) and ribonucleic acid (RNA). Naturally occurring DNA and RNA molecules are typically composed of repeating chemical building blocks called nucleotides which are in turn made up of a sugar (deoxyribose or ribose, respectively), a phosphate group, and one of five bases, adenine (A), cytosine (C), guanine (G), and thymine (T) or uracil (U). The human genome, for example, contains approximately three billion nucleotides of DNA sequence and an estimated 20,000 to 25,000 genes. DNA sequence information can be used to determine multiple characteristics of an individual as well as the presence of and or susceptibility to many common diseases, such as cancer, cystic fibrosis, and sickle cell anemia.

As the genomic and proteomic knowledge base expands, so does the need for methods to collect, understand, and apply biologically relevant information. The drive towards personalized medicine magnifies these needs. Methods, such as analyses using microarrays that allow the use of small volumes of sample for highly multiplexed analysis of a plurality of components are valuable tools. Methods that provide for the controllable automated manufacture of arrays derive value from these same biomedical detection and analysis goals.

DETAILED DESCRIPTION OF THE INVENTION

Embodiments of the invention provide methods and devices that allow the progress and fidelity of solid-phase electrochemical polymer synthesis to be monitored. Methods are provided that can be used to synthesize, cleave, and analyze samples immobilized on electronic sensors. The methods allow for selectivity and control in the monitoring of fidelity and progress of solid-phase synthesis reactions and also for enhancements in the pace in which polymers can be synthesized and cleaved from a surface. Methods according to embodiments of the invention are additionally applicable to creating arrays of polymers on a substrate.

Synthesis reactions generally create impurities or unwanted products in addition to the desired products. For example, in polymer synthesis reactions that proceed by stepwise incorporation of monomers, unwanted products may be created when a growing polymer fails to add the next monomer. When the growing polymer fails to add the next monomer, polymers are created that are truncated and or have an incorrect sequence. Additionally, other unwanted products may be obtained through decomposition reactions and other unexpected reactivity. It can be desirable to understand the chemical make up and fidelity of a polymer array that is being used, for example, in an assay in order to have confidence about the results of the assay. A negative assay result, such as, a failure to detect the presence of an analyte, could be attributed to absence of analyte in the sample, or in the alternative to failure of the probes to behave as expected. In the absence of confidence about the fidelity of the assay materials, results obtained can be difficult to interpret.

In general, a probe or probe molecule is a small molecule or biomolecule capable of undergoing a binding or molecular recognition event with a target molecule. Molecular recognition is a specific interaction between molecules. Examples of molecular recognition events are receptor-ligand, antibody-antigen, sugar-lectin, DNA-protein, and nucleic acid hybridization reactions. A target or target molecule refers to a molecule or biomolecule that is specifically recognized by a probe molecule through a molecular recognition event. In the case of nucleic acids, a molecular recognition event occurs when nucleic acids hybridize to complementary nucleic acids.

Figure 1:
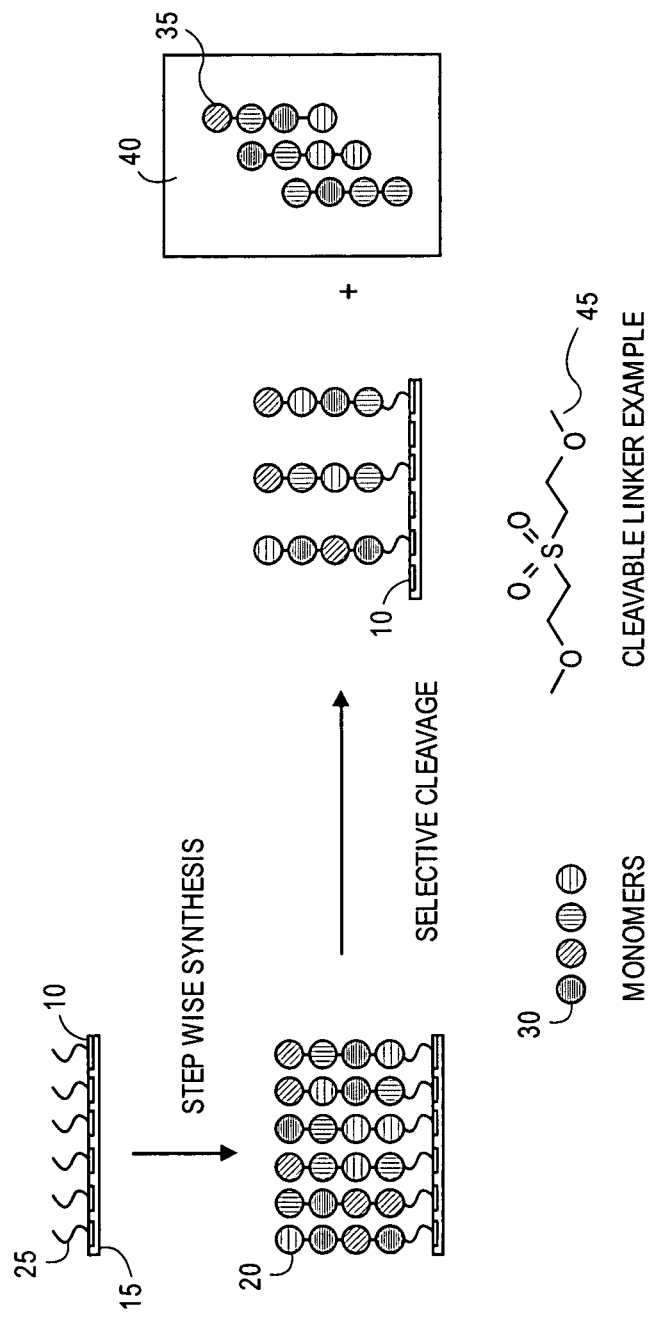
FIG. 1 diagrams a solid-phase synthesis process in which a polymer is synthesized on an electrode and the synthesized polymers are cleaved from the electrode.

FIG. 1 provides a general scheme for synthesizing a polymer on a substrate in a manner that allows the polymer to be selectively and controllably cleaved from the substrate. In FIG. 1, electrodes 10 are housed in a substrate 15 and operably connected to electronic components (not shown) that allow the controllable synthesis and or detection of polymers 20 on the electrode 10 surface. Electrodes 10 comprise an array of electrodes. Before polymer synthesis or attachment to the electrode 10 surface, the electrode 10 surface is functionalized with a cleavable linker 25. As described more fully herein, the polymer 20 can be synthesized on the electrode 10 surface by adding monomers 30 in a stepwise manner. The polymers can be synthesized, for example, using an electrochemically generated acid that deprotects a growing polymer chain and allows the addition of a monomer to the chain. Monomers (polymer building blocks) include nucleotides and amino acids, as described more fully herein. Some, but not all, electrodes 10 are selectively activated to cause synthesized polymers 20 to be cleaved from the surface. After selective cleavage, some electrodes 10 have polymers 20 attached and some do not have polymers 20 attached. Selective cleavage occurs, for example, through the direct reduction or oxidation of the linking molecule or through reduction or oxidation of a second molecule that after reduction or oxidation is activated toward a second reaction that causes the cleavage of the linking molecule. For example, the second molecule is a molecule that is capable of undergoing oxidation or reduction and of generating an acid or a base after oxidation or reduction. In the present example, the polymers have been synthesized using electrochemically generated acid, so the cleavable linker is cleaved using an electrochemically generated base or a linker that cleaves upon reduction, for example. The electrochemically generated base then causes the linking molecule to cleave and the polymer is separated from the surface. The activation of an electrode 10 to cause the cleavage of the polymer molecules that are attached to the electrode can be done in a highly selective manner so that only electrodes 10 that are selected and activated have the polymers 20 cleaved from their surfaces. The cleaved polymers 35 that are no longer attached to the substrate 15 are free in solution 40 and are available for further analysis or use. An exemplary cleavable linker 45 is shown. This linker can be cleaved by exposure to a basic solution.

Figure 2:
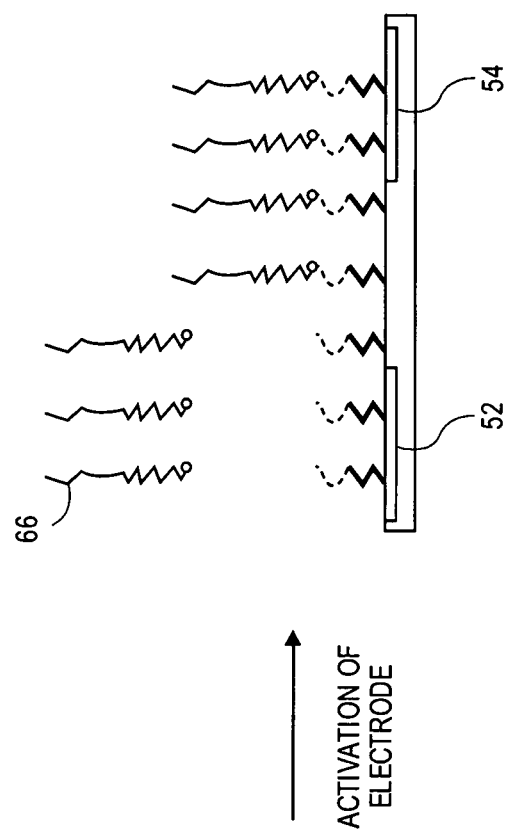
FIG. 2 diagrams the release of polymers from an exemplary electrode array surface that has attached cleavable polymers that incorporate a label.
Figure 2:
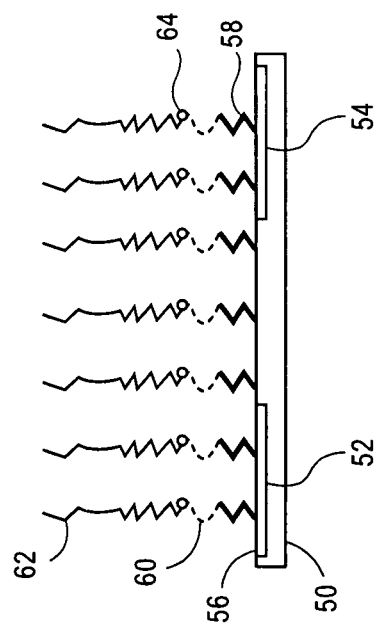

FIG. 2 provides an exemplary electrode array having cleavable polymers attached. In FIG. 2, a substrate 50 houses electrodes 52 and 54 that are operably connected to electronics (not shown) that allow the application of voltage and or current to the electrode and the sensing of solution resistance by the electrode. The substrate surface 56 has a layer of metal hydroxide that allows attachment of polymers. The substrate surface 56 is functionalized with a silane linking molecule 58. The silane linking molecule 58 is coupled to a cleavable linker 60. A polymer 62 having a label 64 is coupled to the cleavable linker 60. The polymer 62 can be built on the cleavable linker 60 through electrochemical synthesis and stepwise monomer coupling. As described more fully herein, the label 64 is a label that is detectable by spectroscopic methods such as, for example, UV-vis, fluorescence spectroscopy, radiation (radioactivity) detection, isotope detection, surface plasmon resonance, and Raman spectroscopy. Common labels that can be detected include fluorescent molecules, radioactive labels, q-dots, and nanoparticle reporters. The label can be incorporated into the growing polymer chain by adding a monomer having a label. An electrode 52 is selectively activated and polymers 66 having attached label 64 are released from the electrode surface into solution. The released polymers 66 are available in solution for further analysis or use. Although in this example the label is shown as proximal to the cleavable linker, a label can be incorporated at other locations in the polymer and does not necessarily have to be proximal to the cleavable linker.

In general, a cleavable linker is a molecule that is capable of linking a polymer to a substrate surface. The cleavable linker is cleaved under selective conditions, so that under one set of conditions a cleavable linker links the polymer molecule to the substrate surface, but under a second different set of conditions it releases the polymer from the substrate surface. For example, the cleavable linker can be stable under neutral and acidic conditions, but cleaves under basic conditions. Alternatively, the cleavable linker is stable under basic and neutral conditions, but cleaves under acidic conditions. Additionally, cleavable linkers can be used that cleave upon reduction or oxidation or photo-activation (in the presence of certain wavelengths of light). In the case of polymer synthesis that employs an electrogenerated acid requiring an oxidizing potential to generate the acid, a linker is chosen that cleaves under more reducing conditions than the oxidizing potential of the electrogenerated acid. Other schemes are possible wherein the cleavable linker is stable under synthesis conditions, but capable of cleaving under different select conditions.

Figure 3:
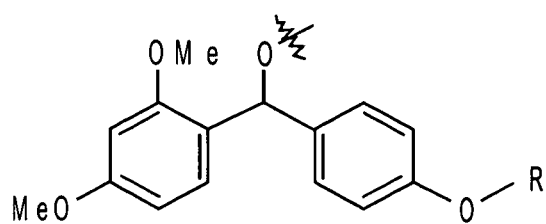
FIG. 3 provides exemplary molecules that are capable of functioning as cleavable linkers.
Figure 3:
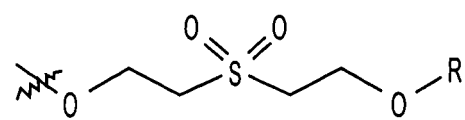
Figure 3:
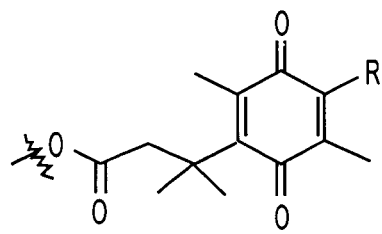
Figure 3:
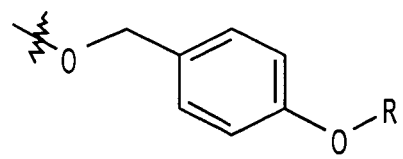

FIG. 3 provides some exemplary cleavable linkers that can be used in the electrochemical synthesis of nucleic acids, peptides, small molecules, and carbohydrates and their chimeric forms. By passing current through individual electrodes, different chemistry conditions can be created in situ for specific applications. For example, an acid can be generated locally in the region near the electrode for a linker that is cleavable under acidic conditions by applying a potential to the electrode in the presence of an acid-generating species. Additionally, basic conditions can be created for linkers that are cleaved under basic conditions (by applying a potential to the electrode in the presence of a base-generating species), reductive conditions can be created for linkers that are cleaved upon reduction, and oxidative conditions can be created for linkers that are cleaved upon oxidation. In general, a cleavable linker is chosen so that the conditions used to cause the linker to cleave are compatible with the polymer being synthesized and the synthesis conditions used to synthesize the polymer. For example, if acidic conditions are used to couple monomers to the growing polymer chain, a linker that is cleavable under basic conditions or by oxidation or reduction can be chosen. An exemplary reduction cleavable linker such as the one shown in FIG. 3, is described in "Biomolecular Surfaces that Release Ligands Under Electrochemical Control," *J. Am. Chem. Soc.*, 112:4235 (2000). A variety of cleavable linkers exist and some further examples include, the linkers discussed in "Linker Phosphoramidite Reagents for Oligonucleotide Synthesis on Underivatized Solid-phase Supports," Tetrahedron Letters, 42:8943 (2001). Additionally, electrochemically synthesized polymers can be cleaved from a substrate surface using photocleavable linkers. Exemplary photocleavable linkers are described in "Photocleavable Peptide-DNA Conjugates: Synthesis and Applications to DNA Analysis Using MALDI-MS," *Nucleic Acids Res.*, 27:4626 (1999).

Figure 4:
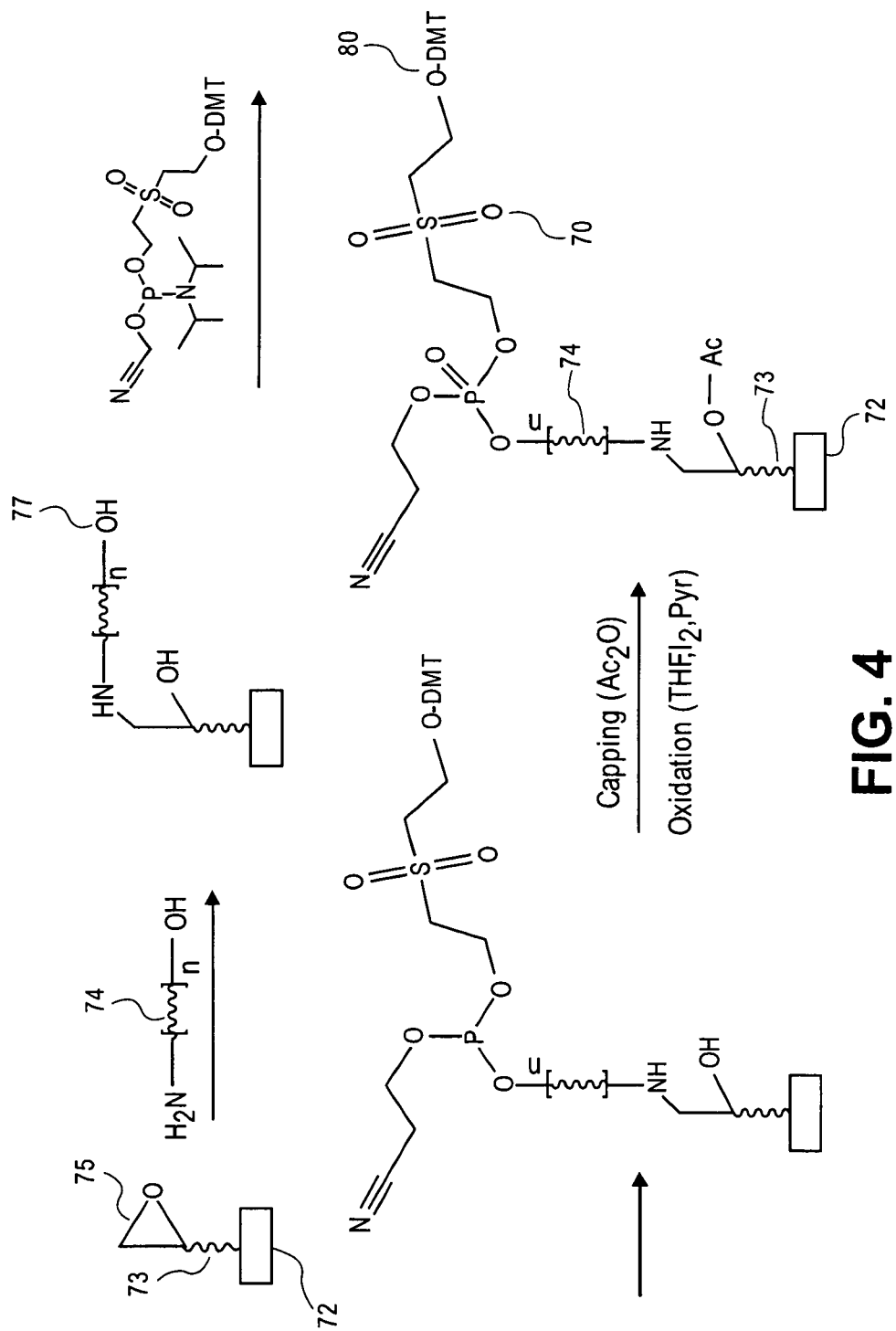
FIG. 4 shows a method for attaching an exemplary cleavable linker to a substrate.

FIG. 4 illustrates the attachment of a base cleavable linker to a substrate surface. In the example of FIG. 4, a cleavable linker (a base cleavable linker) 70 is attached to substrate 72, an electrode, (not shown to scale) through a silane linker 73 and flexible linker (e.g., polyethylene glycol (PEG)) 74. To attach the cleavable linker to the substrate surface 72, a silane linker can be used that carries an epoxyl group 75, such as glycidoxipropyltrimetiloxisilane. The epoxyl group 75 of the surface-attached silane linker can be opened to form a covalent bond upon reaction with an amine group of a flexible linker, in this embodiment the linker is poly ethylene glycol, 74. The substrate-attached flexible linker presents a hydroxyl group (—OH) 77 for coupling of the cleavable linker using standard amidite chemistry. A standard capping and oxidation reactions as part of the amidite chemistry to attach the cleavable linker to the substrate is performed resulting in an electrode functionalized with cleavable linker 70 carrying a dimethoxytrityl (DMT) protected hydroxyl group 80. For acid and base cleavable linkers, it is also possible to cleave the linkers from the surface of an electrode or an array of electrodes by applying the base or acid that induces cleavage to the surface of the array. By washing the surface of an electrode or an array having acid or base cleavable linkers with an acidic or basic solution that induces cleavage, cleavage of polymers from the surface of the array in a non-specific manner can be achieved.

Figure 5:
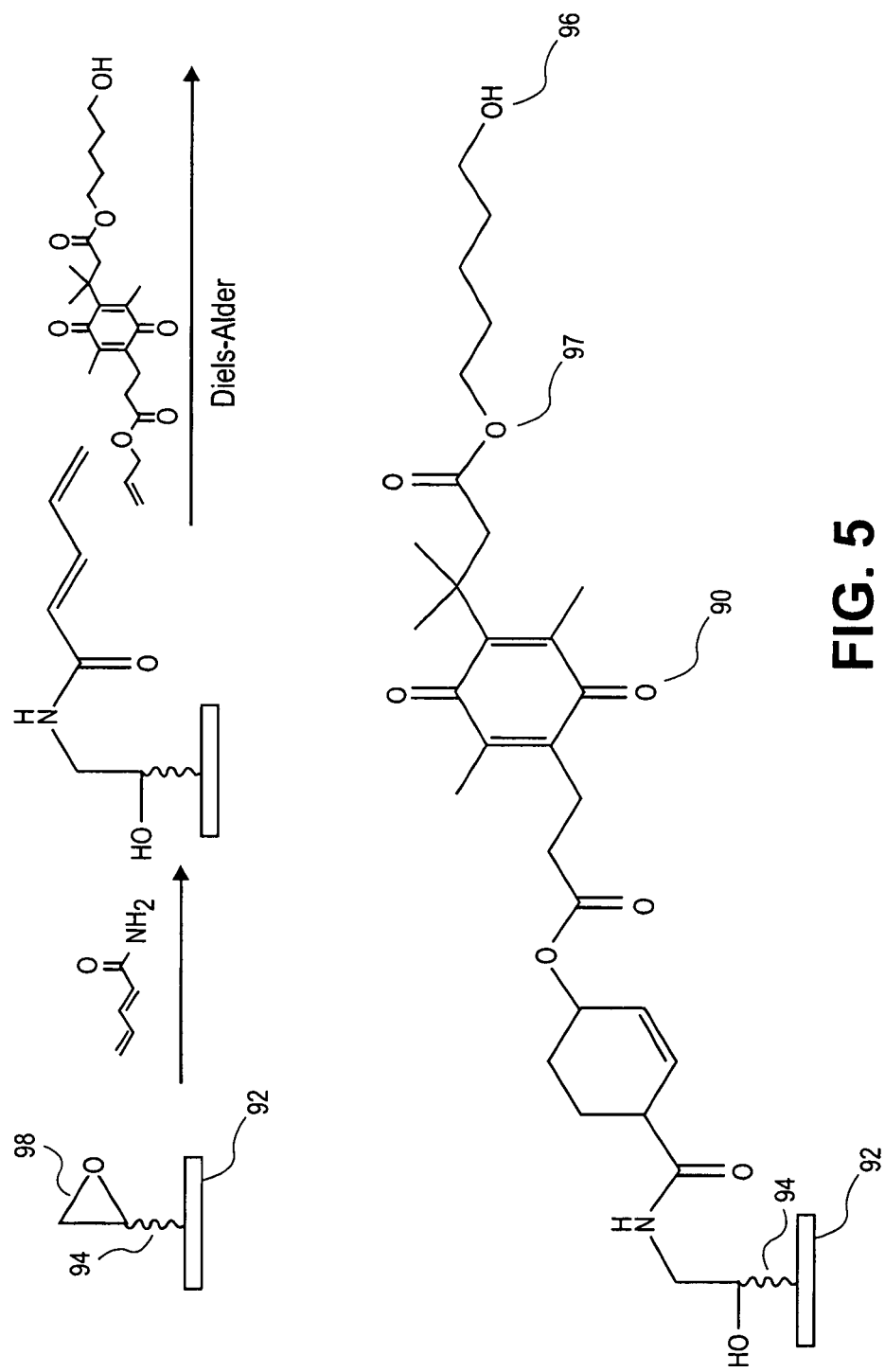
FIG. 5 shows a method for attaching an exemplary cleavable linker to a substrate.

In an additional example of the attachment of a cleavable linker to a substrate surface, FIG. 5 shows a second exemplary cleavable linker (a reduction cleavable linker) 90 attached to substrate 92 (not shown to scale) through silane linker 94. The substrate-attached cleavable linker 90 presents a hydroxyl group (—OH) 96 for further molecular coupling and a cleavage point 97. The substrate 92, as discussed herein, is typically an electrode. To attach the cleavable linker to the substrate surface 92, a silane linker can be used that carries an epoxyl group 98, such as glycidoxipropyltrimetiloxisilane, to attach the cleavable linker to the surface. The epoxyl group 98 of the surface-attached silane linker can be opened to form a covalent bond upon reaction with a hydroxyl group or an amine group of a cleavable linker, thereby attaching the linker to the substrate surface. In this example, the epoxide 98 is reacted with an amide containing diene. The resulting diene-containing surface is coupled to the cleavable linker through a Diels-Alder reaction. Alternatively, cleavable linkers can be attached to the substrate surface through standard solid phase coupling chemistry used, for example, in DNA or peptide synthesis processes. For example, molecules presenting an available phosphoramidite are coupled to an available hydroxyl group attached to a substrate surface. In this example, the available hydroxyl group can be presented by a silane linker molecule.

In general, a polymer growth site is a surface-attached chemical functional group that allows the addition of a monomer, linker, or other polymeric unit to the surface of the substrate. The polymer growth site could be the reactive functional group (that allows molecular addition or coupling) of a silane linker molecule, a linker molecule, a cleavable linker molecule, or a growing polymer chain, for example. The polymer growth site may be protected or unprotected.

An array is an intentionally-created collection of molecules housed on a solid support in which the identity or source of a group of molecules is known based on its location on the array. The molecules housed on the array and within a feature of an array can be identical to or different from each other. A macroarray generally contains feature sizes of about 300 μm or larger and can be imaged by gel and blot scanners. A micro array generally has feature sizes of less than 300 μm.

The features, regions, spots, or sectors of an array may have any convenient shape, for example, circular, square, rectangular, elliptical, or wedge-shaped. In some embodiments, the region in which each distinct molecule is synthesized within a sector is smaller than about 1 mm$^2$ or less than 0.5 mm$^2$. In further embodiments the regions have an area less than about 10,000 μm$^2$ or less than 2.5 μm$^2$. Additionally, multiple copies of a polymer are located within any region. The number of copies of a polymer can be in the thousands to the millions within a region. In general, an array can have any number of features, and the number of features contained in an array may be selected to address such considerations as, for example, experimental objectives, information-gathering objectives, and cost effectiveness. An array could be, for example, a 20×20 matrix having 400 regions, 64×32 matrix having 2,048 regions, or a 640×320 array having 204,800 regions. Advantageously, the present invention is not limited to a particular size or configuration for the array.

A solid support, support, or substrate is an object having a rigid or semi-rigid surface or surfaces. In some aspects at least one surface of a solid support is planar or substantially planar. The features of an array optionally form synthesis regions that are for example, wells, depressions, raised regions, pins, or etched trenches. In embodiments of the invention the substrate comprises a silicon wafer or a portion of a silicon wafer. A silicon wafer may also be referred to as a chip or a semiconductor substrate. A wafer or chip may be fashioned in various shapes and sizes. The chip can be overlaid or embedded with circuitry for driving electrodes, sensing voltages, microprocessors, memory functions, and input/output capabilities. In embodiments of the invention, the chip comprises at least surface-accessible electrodes and embedded circuitry for individually addressing and driving the electrodes and sensing voltages, currents, and or resistances and or circuitry capable of connecting the electrodes to external mechanisms for individually addressing the electrodes, sensing voltages, currents, and or resistances, and driving the electrodes. A substrate may also be comprised of silicon, glass, nylon, plastic or other polymeric material, silicon nitride, metals, metal oxides, metal nitrides, or combinations thereof.

Polymers that have been cleaved from an electrode surface through the cleavage of a cleavable linker can be analyzed by a variety of methods. For example, cleaved polymers, such as nucleic acids or peptides, can be collected, concentrated and separated using HPLC (high performance liquid chromatography), and the fractions analyzed for polymer content. If the polymers bear a label, detection of the polymers, especially at low concentrations can be facilitated through the detection of the label. Cleavable linkers can be placed at all synthesis sites on an electrode array or only on selected sites. Since, typically an electrode has a small surface area, the number of polymers synthesized on the surface can be limited. In this case, samples from multiple arrays and or multiple electrodes can be combined for analysis. Additionally, radioactive labeling can be used when the quantity of sample to be detected is limited.

Many substrate and electrode materials, such as metals, metal oxides, and $SiO_2$, have surface-attached —OH groups that are available for further reaction and molecular coupling. Further, surfaces that present —OH groups for molecular coupling can be created on substrate surfaces, through, for example, creating a thin oxide layer on a metal (such as through chemical or plasma etching processes) or through depositing a thin layer of $SiO_2$ onto the surface. If the substrate surface is $SiO_2$, the surface has been coated with $SiO_2$, or the surface is a metal having available —OH groups, molecules are optionally attached to the sensor surface through the use of silane linkers (organo silane compounds). In general, silane linkers are molecules that contain silicon. Useful silane molecules include ones that have at least two different reactive groups bonded to the silane atom of the molecule: Y—R—Si—(X)$_2$. One of the reactive groups, the group represented as X, is capable of bonding to inorganic materials such as glass ($SiO_2$) and metals. These functional groups that are capable of bonding to inorganic materials are groups such as methoxy, ethoxy, chlorine, and silanolic hydroxyl groups. The second functional group, the group represented as Y, is a group such as a vinyl, an epoxy, a methacryl, an amino, a mercapto, or a carboxylic acid group that is capable of forming a chemical bond to an organic material (such as a monomer used to form a polymer). The R group is typically an organic group comprised of from 1 to 10 carbon atoms, such as a straight chain or branched alkane. For example, a silanating agent, such as hydroxypropyltriethoxysilane can be vapor deposited or supplied in a solution to the surface to be silanated. After reaction, the surface presents a —OH group for further molecular coupling. Metal surfaces such as nickel, palladium, platinum, titanium dioxide, aluminum oxide, indium tin oxide, copper, iridium, aluminum, titanium, tungsten, rhodium or other surface having available hydroxy groups or other similar surface groups can also be silanated for further attachment of molecules. In one embodiment of the invention, the surface is a platinum electrode. A very thin layer of oxide can be created on a metal surface, for example, by etching the metal surface with an oxygen plasma or through damascene processes.

An array of electrodes can be equipped with circuitry for individually addressing the electrodes, driving the electrodes at selected voltages (or set current values corresponding to the desired voltage), memory for storing voltage current information to be supplied to the electrodes, memory and microprocessors for measuring electrode characteristics, differential amplifiers, field effect transistors (direct and floating gate). Alternatively, one or more of these functions can be performed by an attached computer system.

Figure 6:
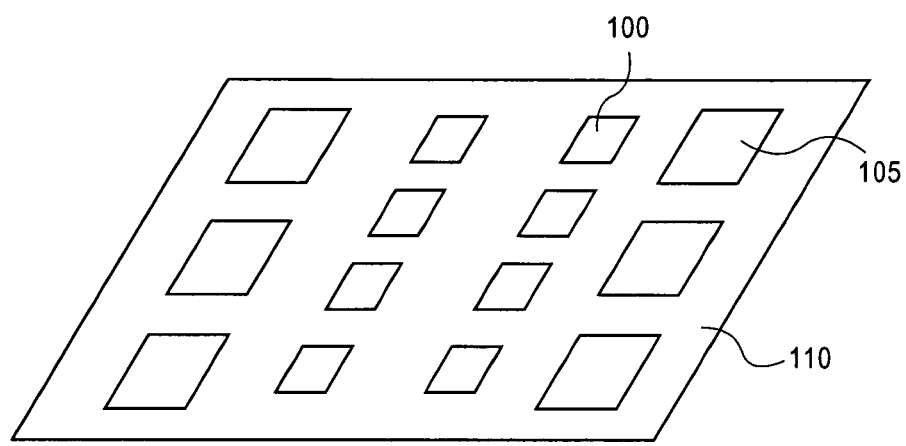
FIG. 6 is a simplified diagram of an exposed electrode array that can be used to synthesize polymers on the electrodes and to detect molecular recognition events using the array of electrodes.

FIG. 6 provides a simplified diagram showing an array of exposed sensing and reference electrodes 100 and drive electrodes 105 on a substrate 110. In this example, the electrodes are used both for synthesizing polymers and also for molecular sensing. Nucleic acids, peptides, and or other types of affinity probes (not shown) are attached to the sensing and or reference electrodes. The reference electrode may or may not have a similar or different affinity probes attached. The sensing electrodes optionally have a plurality of probe molecules attached and the probe molecules attached to one sensing electrode are different from the probe molecules attached to a different sensing electrode. Drive electrodes 105 are typically larger in surface area than the micron or sub-micron scale sensing and reference electrodes 100. Electronics associated with driving the electrodes and signal handling (sensing and referencing capacity) (not shown) are located in the substrate 110. An integrated charge value from an electrode is converted to a voltage value through a two stage amplifier. An internal (not exposed) monolithic NMOS or metal-insulator-metal capacitor is optionally connected to the amplifier via an internal switch and used as a reference capacitor.

The electrodes of the array are used to synthesize polymers. For synthesis the electrodes are used to create an acidic or basic region around the electrode surface. The acid or base causes deprotection of the growing polymer chain and allows monomer addition. Optionally, confinement electrodes of opposite polarity or floating separate attachment electrodes are provided to confine the acid or basic region produced and prevent drift to surrounding electrodes that may not be activated for synthesis. Further optionally, a set of two latches are provided at each electrode capable of being activated for polymer synthesis to allow the electrode to exist in multiple states: driven by a first voltage, driven by a second voltage, or floated during the synthesis cycle.

Voltage sources for the electrodes can be internally multiplexed from external source(s) through digital control and can optionally be applied in parallel to a large array of electrodes. In operation, voltages are applied to a programmed selection of electrodes in the presence of an acid-generating reagent as a solution containing a monomer is supplied to the exposed electrodes. The applied voltage creates an acidic region near the activated electrode (through the generation of an electro-generated acid, or EGA) and allows polymer growth on the activated electrode. Through selection of electrodes and choice of monomer to supply, polymers of known desired sequence are synthesized at the electrodes.

Electrochemical reagents are reactive species that can be generated electrochemically at an electrode through an oxidation or reduction process. Electrochemical reagents can be generated at an electrode by supplying a minimum voltage that corresponds with the oxidation or reduction potential of the desired species in solution. Reagents that are acids ($H^+$) and bases (such as $OH^-$) can be generated electrochemically. Molecules that can be used to generate an acid electrochemically that can used to deprotect a growing nucleic acid polymer attached to an electrode surface (e.g., remove a DMT group) include, for example, hydroquinone that is converted to benzoquinone upon oxidation thereby releasing two protons ($H^+$) and a hydroxyanthraquinone that is converted to anthraquinone upon oxidation thereby releasing two protons ($H^+$) (a non-aqueous system) (this occurs typically between 0.8 to 2.0 V). Electrogenerated bases include, for example, azobenzene and its derivatives. Azobenzenes typically yield electrogenerated bases between −1.0 to −2.0 V (in organic solutions). Molecules that can be used to generate a base in solution electrochemically include, for example, azobenzene, anthraquinone, aromatic halides (where the halide is iodine or bromine), and carbon disulfide.

An electrochemical reagent can be generated at a solution-accessible electrode by applying sufficient electrical potential to an electrode. The electrochemical reagent is capable of removing a protecting group from the growing end of a polymer being synthesized on the electrode. In hydroquinone/benzoquinone example, the electrochemical reagent produced ($H^+$) is a deprotecting agent. In other reactions, the electrochemical reagent may be an intermediate in the formation of the deprotecting agent.

In general, nucleic acids include polymers of deoxyribonucleotides (DNA) or ribonucleotides (RNA) and analogs thereof that are linked together by a phosphodiester bond. A polynucleotide can be a segment of a genome, a gene or a portion thereof, a cDNA, or a synthetic polydeoxyribonucleic acid sequence. Polynucleotides and nucleic acid polymers refer to polymeric forms of nucleotides and nucleotide analogs that comprise purine and pyrimidine bases, or other natural, chemically or biochemically modified, non-natural, or derivatized nucleotide bases, of any length. Polynucleotide and nucleic acid also refer to non-natural analogs of nucleic acids, such as peptide nucleic acids (nucleic acids with peptide backbones), and polyamide polynucleotides. An oligonucleotide is a polynucleotide having from 2 to 20 nucleotide monomer units. The length chosen for a probe nucleic acid depends on several factors, including G/C content of the sequence, positioning of mismatched bases (if any), degree of uniqueness of the sequence as compared to the population of target nucleotides, the chemical nature of the polynucleotide (e.g., methylphosphonate backbone and phosphorothiolate), desired conditions for hybridization reaction (e.g., temperature and ionic strength of the solution). Typically a probe molecule will be at least 5 nucleotides and less than 75 nucleotides in length. Preferably the probe is between 24 and 56 nucleotides in length.

A polynucleotide, including an oligonucleotide, can contain nucleotide analogs, or a backbone bond other than a phosphodiester bond. In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide or oligonucleotide also can contain nucleotide analogs, including methylated nucleotides, non-naturally occurring synthetic nucleotides or modified naturally occurring nucleotides.

The covalent bond linking the nucleotides of a polynucleotide generally is a phosphodiester bond (the sugar-phosphate backbone). However, the covalent bond also can be any of a number of other types of bonds, including a thiodiester bond, an O-methyl phosphate, a phosphorothioate bond, a peptide-like amide bond or any other bond known to those in the art as useful for linking nucleotides to produce synthetic polynucleotides. The incorporation of non-naturally occurring nucleotide analogs or bonds linking the nucleotides or analogs can be particularly useful where the polynucleotide is to be exposed to an environment that can contain nucleolytic activity, since the modified polynucleotides can be less susceptible to degradation.

Figure 7:
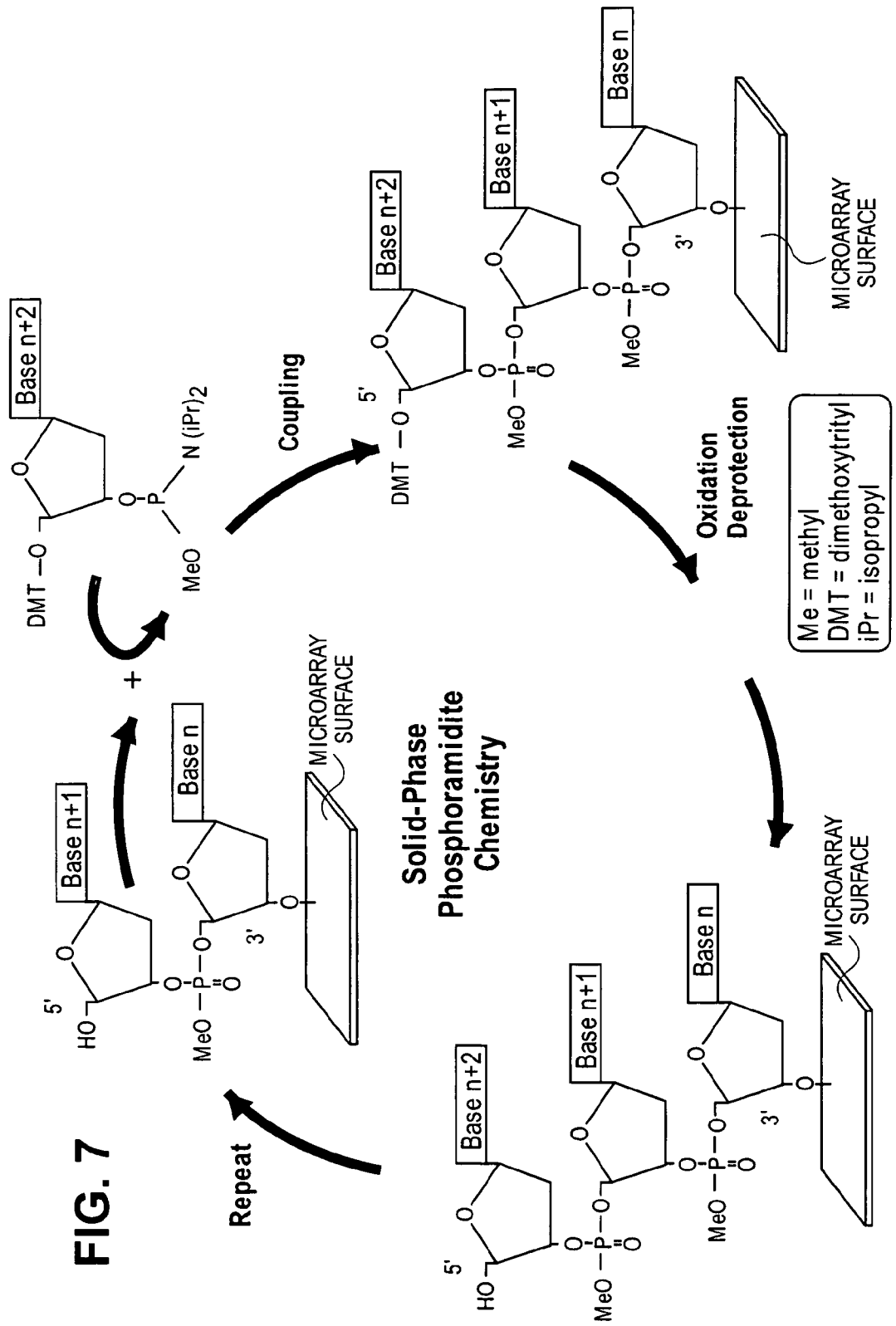
FIG. 7 diagrams a method for solid-phase nucleic acid synthesis that can be used to controllably build nucleic acid molecules having a desired sequence on a solid surface.

A monomer addition cycle is a series of chemical reactions that result in the addition (or covalent attachment) of a monomer to a growing polymer chain or linker molecule. For example, the following steps typically comprise a common method used to synthesize a polynucleotide on a solid support (i.e., phosphoramidite-based solid phase polynucleotide synthesis). Referring now to FIG. 7, a first step in the polynucleotide synthesis is the deprotection of the surface-attached polymer growth site through removal of the DMT group from, for example, a 5'-protected nucleotide wherein the 5'-hydroxyl is blocked through the covalent attachment of DMT. The deprotection is accomplished using a protic acid (for example, a protic acid such as trichloroacetic acid or an electrochemically generated acid). The substrate optionally is then washed to remove the cleaved protecting group and other reagents and mobile reaction products (with, for example, acetonitrile). A molecule, such as a phosphoramidite nucleotide, optionally activated with tetrazole, is then coupled to the surface-attached deprotected molecule. Optionally unreacted surface-attached deprotected molecules are capped to prevent further participation in subsequent monomer addition cycles. The trivalent phosphate trimester linkage is converted to a pentavalent phosphate triester through oxidation with, for example, iodine, and the pentavalent phosphate triester is converted to a phosphodiester through reaction with ammonium hydroxide.

A protecting group is a chemical functional group that is designed to block a reactive site in a molecule, but that may be removed upon exposure to an activator or a deprotecting reagent. When the protecting group is removed, the reactive site is more readily available to react and form chemical bonds. A deprotecting agent is an agent that can remove a protecting group from a molecule leaving the reactive site available for further chemical reaction. Deprotecting reagents include, for example, acids, bases, free radicals, and electromagnetic radiation. Protecting groups can be bound to a monomer, a polymer, a linker molecule or a monomer, or polymer, or a linker molecule attached to a solid support to protect a reactive functionality on the monomer, polymer, or linker molecule. Hydroxyl groups on phosphoramidites may be protected by dimethoxytrityl (DMT), which is acid labile (removable). Exocyclic amine groups on nucleotides, in particular on phosphoramidites, are preferably protected by dimethylformamidine on the adenosine and guanosine bases, and isobutyryl on the cytosine bases, both of which are base labile protecting groups. This protection strategy is sometimes known as fast oligonucleotide deprotection (FOD). Methods for solid phase DNA synthesis are described in, for example, *Nucleic Acids Research,* 20:1265 (1992).

Any unreacted deprotected chemical functional groups may be capped at any point during a synthesis reaction to avoid or to prevent further bonding at the selected molecule. In general, capping reagents are agents that prevent further chain growth at the site of polymer chain formation such as, for example, an acid anhydride without further reactive functionalities. Capping groups cap deprotected functional groups by, for example, binding with the unreacted amino functions to form amides. Capping agents suitable for use in an embodiment of the invention include: acetic anhydride, n-acetylimidizole, isopropenyl formate, fluorescamine, 3-nitrophthalic anhydride and 3-sulfopropionic anhydride.

In an alternate embodiment, the polymers created on one or more electrodes comprising the array are peptides. In general, peptides are polymers of amino acids, amino acid mimics or derivatives, and/or unnatural amino acids. The amino acids can be any amino acids, including $\alpha$, $\beta$, or $\omega$-amino acids and modified amino acids. When the amino acids are $\alpha$-amino acids, either the L-optical isomer or the D-optical isomer may be used. In general, an amino acid contains an amine group, a carboxylic group, and an R group. The R group can be a group found on a natural amino acid or a group that is similar in size to a natural amino acid R group. Additionally, unnatural amino acids, for example, O-alanine, phenylglycine, homoarginine, aminobutyric acid, aminohexanoic acid, aminoisobutyric acid, butylglycine, citrulline, cyclohexylalanine, diaminopropionic acid, hydroxyproline, norleucine, norvaline, ornithine, penicillamine, pyroglutamic acid, sarcosine, and thienylalanine are also contemplated by the embodiments of the invention. These and other natural and unnatural amino acids are available from, for example, EMD Biosciences, Inc., San Diego, Calif.

A peptide is a polymer in which the monomers are amino acids, a group of molecules which includes natural or unnatural amino acids, amino acid mimetics, and amino acid derivatives, which are generally joined together through amide (peptide) bonds. A peptide can alternatively be referred to as a polypeptide. Peptides contain two or more amino acid monomers, and often more than 50 amino acid monomers (building blocks).

Figure 8:
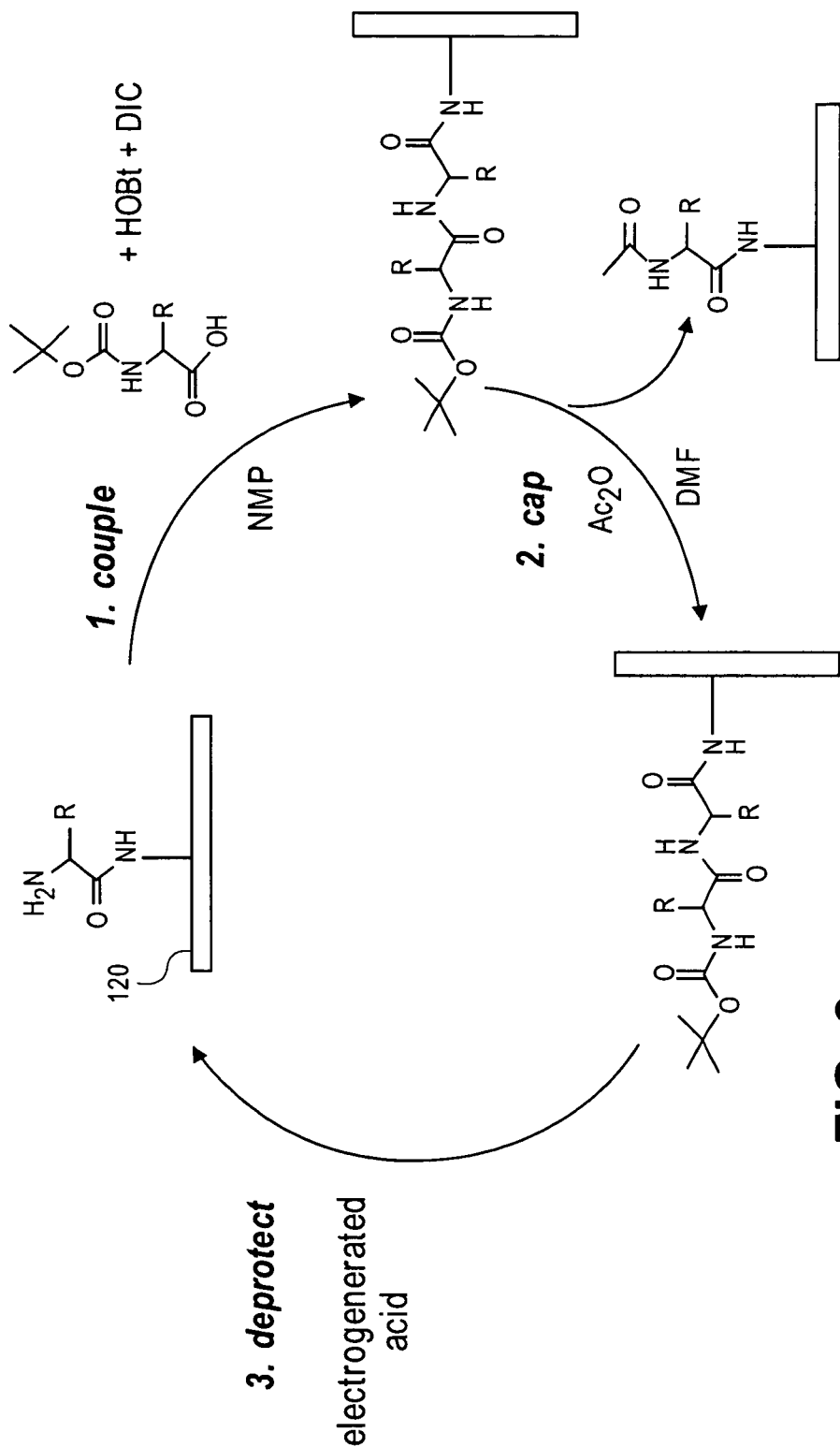
FIG. 8 diagrams a method for solid-phase peptide synthesis that can be used to controllably build peptide molecules having a desired sequence on a solid surface.

FIG. 8 shows a general scheme for solid-phase peptide synthesis in which an electrogenerated acid is used to cleave a protecting group from a polymer growth site. In FIG. 8, an electrode surface 120 is provided having, in this example, a first unprotected amino acid attached to the surface as the polymer growth site. The polymer growth site could alternatively also be the unprotected functional group of a silane linker molecule, a linker molecule, or a cleavable linker molecule, for example. A second amino acid having an amino protecting group is coupled to the first amino acid. In this example, the second amino acid is N-protected with a BOC protecting group. The coupling reaction is performed in a solution of 1-hydroxybenzotriazole (HOBt) and diisopropylcarbodiimide (DIC) in N-methyl pyrrolidone (NMP). Unreacted amine groups are capped using an acetic anhydride ($Ac_2O$) solution in dimethylformamide (DMF). The substrate surface is then provided with a solution containing a molecule capable of generating an acid electrochemically. Upon activation of the electrode on which the growing polymer chain is attached, an electrochemically generated acid is produced and the N-protecting group is removed from the attached peptide. A solution containing the next desired amino acid is supplied to the electrode surface and the next desired amino acid is coupled to the growing polymer chain. By repeating the process shown in FIG. 8, peptides of desired sequence and length in selected electrodes upon the substrate surface can be produced. Typically, polymers containing from about 2 to about 50 mers (polymeric units or amino acids) are useful as probes. Useful molecules capable of electrochemically generating an acid include hydroquinone and 1,2-diphenylhydrazine (which operates around −3.0V in non-aqueous solution).

In other embodiments, the cleaving process leading to the removal of the protecting groups from the polymer growth site may, for example, be acid-catalyzed cleavage or base-catalyzed cleavage. The chemistry of the process will depend on the type of protecting groups and on the type of cleaving reagents that are electrochemically generated in solution. For example, if the protecting group is t-BOC, acid cleavage can be used. If the protecting group is FMOC, for example, then base cleavage can be used.

The deprotected polymer growth sites are available for further reaction, such as for example, a peptide-bond forming coupling reaction whereas the molecules that retain their protective groups on polymer growth sites are not available for further reaction. Solid phase peptide synthesis can be carried out using standard techniques, see for example, Bodansky, M., Bodansky, A., *The Practice of Peptide Synthesis* ($2^{nd}$ edition), Springer Verlag, Berlin (1995); Stewart, J. M., Young, J. D., *Solid Phase Peptide Synthesis* ($2^{nd}$ edition), Pierce Chemical Company, Rockford Ill., (1984); *Solid-Phase Peptide Synthesis: Methods in Enzymology*, vol. 298, Academic Press (1997); and for synthesis of peptides and peptidomimetics: *Methods in Organic Chemistry*, vol E22, Houben Weyl (2004).

Any unreacted deprotected chemical functional groups may be capped at any point during a synthesis reaction to avoid or to prevent further bonding at such molecule. In general, capping reagents can be a reagent that prevents further reactivity at the site of polymer chain formation such as, for example, an acid anhydride without further reactive functionalities. Capping groups cap deprotected functional groups by, for example, binding with the unreacted amino functions to form amides. Capping agents suitable for use in an embodiment of the invention include: acetic anhydride, n-acetylimidizole, isopropenyl formate, fluorescamine, 3-nitrophthalic anhydride and 3-sulfoproponic anhydride.

Protecting groups useful in solid-phase peptide synthesis that protect peptide amine groups include, for example, a t-butoxycarbonyl (t-BOC or BOC) or benzyloxycarbonyl (CBZ), both of which are acid labile, or by 9-fluorenylmethoxycarbonyl (FMOC), which is base labile. Additional protecting groups that may be used in accordance with embodiments of the invention include acid labile groups for protecting amino moieties: tert-amyloxycarbonyl, adamantyloxycarbonyl, 1-methylcyclobutyloxycarbonyl, 2-(p-biphenyl)propyl(2)oxycarbonyl, 2-(p-phenylazophenylyl)propyl(2)oxycarbonyl, .alpha.,.alpha.-dimethyl-3,5-dimethyloxybenzyloxy-carbonyl, 2-phenylpropyl(2)oxycarbonyl, 4-methyloxybenzyloxycarbonyl, furfuryloxycarbonyl, triphenylmethyl (trityl), p-toluene-sulfenylaminocarbonyl, dimethylphosphinothioyl, diphenylphosphinothioyl, 2-benzoyl-1-methylvinyl, o-nitrophenylsulfenyl, and 1-naphthylidene; as base labile groups for protecting amino moieties: 9-fluorenylmethyloxycarbonyl, methylsulfonylethyloxycarbonyl, and 5-benzisoazolylmethyleneoxycarbonyl; as groups for protecting amino moieties that are labile when reduced: dithiasuccinoyl, p-toluene sulfonyl, and piperidino-oxycarbonyl; as groups for protecting amino moieties that are labile when oxidized: (ethylthio)carbonyl; as groups for protecting amino moieties that are labile to miscellaneous reagents, the appropriate agent is listed in parenthesis after the group: phthaloyl (hydrazine), trifluoroacetyl (piperidine), and chloroacetyl (2-aminothiophenol); acid labile groups for protecting carboxylic acids: tert-butyl ester; acid labile groups for protecting hydroxyl groups: dimethyltrityl. See also, Greene, T. W., *Protective Groups in Organic Synthesis*, Wiley-Interscience, NY, (1981).

Additionally, amino acids bearing labels can be incorporated into the electrochemically synthesized peptide. A variety of labels are possible, such as, labels that are detectable by spectroscopic methods such as, for example, UV-vis, fluorescence spectroscopy, radiation (radioactivity) detection, isotope detection, surface plasmon resonance, and Raman spectroscopy. Fluorescent labels include, for example, fluorescein, Rhodamine, DyLight Fluor and Alexa Fluors. Amino acids having attached detectable labels are commercially available from, for example, Sigma-Aldrich, St. Louis, Mo.

In general, labels are molecules that typically do not provide molecular recognition functionality, but instead provide a detectable signal during analysis, such as spectroscopic analysis. The signal of the label in the analytical technique chosen is typically greater than the signal provided by the molecule to which it is attached. Exemplary fluorescent label molecules include, xanthene dyes, fluorescein, lissamine, phycoerythrin, rhodamine dyes, coumarin dyes, and cyanine dyes (cy3, cy5, cy7, etc.). Examples of label constructs include, radioactive labels (substances containing radioisotopes), isotopic labels, Q dots, metal nanoparticles, and Raman reporter particles. Radioactive labels include, for example, tritium, and isotopic labels include, for example, deuterium, phosphorous 32, carbon 14, sulfur 35, and nitrogen 15. Radioactive labels can be detected through photographic techniques, for example, and isotopic labels can be detected, for example, through mass spectral analysis. Raman reporter particles are metal nanoclusters having an organic molecule absorbed on or within the metal cluster or particle where the organic molecule capable of providing a unique Raman signature. The metal cluster provides a surface for enhancing the Raman signal, and the metal nanocluster provides an intrinsic surface enhanced Raman signal (SERS) from the organic molecule absorbed on or within the cluster. A variety of labeled nucleotides are commercially available from, for example, Jena Bioscience, Jena Germany. Intrinsically fluorescent nucleotide analogs are also possible. Fluorescently labeled nucleotides and fluorescent nucleotides can be incorporated into DNA polymers and oligonucleotides through PCR techniques (polymerase chain reaction).

A fluorescent label molecule or SERS signal is detected using known methods for spectroscopy. Typically ultraviolet light is used to excite the fluorescent label molecule and the fluorescent molecule emits light at a lower energy (sometimes visible light), and the emitted light is detected. The excitation light can be provided by lasers, photodiodes, xenon arc lamps, or mercury vapor lamps. Optics are used to focus the light onto a detector and filter excitation light from emitted light. A monochromator may be used in conjunction with the detector to scan through wavelengths of light. Microarray fluorescence readers are commercially available from, for example, Perkin Elmer Corporation, Waltham, Mass. and Applied Precision, Issaquah, Wash. Raman spectrometers are commercially available from, for example, Perkin Elmer Corporation, Waltham, Mass.

In general, a polymer growth site on a substrate or electrode surface is a region of the substrate or electrode surface that presents an attached molecule having a functional group that is capable of further molecular coupling or attachment. For example, the polymer growth site could be the functional attachment group of a silane linker molecule, a linker molecule, a cleavable linker, or a monomer unit of a growing polymer chain, such as the growing end of a nucleic acid or peptide polymer.

Additionally, a polymer attached to a substrate surface may comprise linker (or spacer) molecules. A linker molecule typically is a molecule inserted into the growing polymer, inserted between a polymer molecule and a cleavable linker, or inserted between the surface of the substrate and a cleavable linker molecule that does not necessarily convey functionality to the a surface-attached polymer, such as molecular recognition functionality, but instead elongates the distance between the substrate surface and the polymer to enhance the exposure (steric availability) of the polymer functionality on the surface of the substrate. A spacer molecule has a chain length of 2 to 30 atoms and is comprised of C, H, O, S, N, and or P. The spacer molecules may be, for example, aryl acetylene, ethylene glycol oligomers containing 2-10 monomer units (PEGs), diamines, diacids, amino acids, and polypeptides and polymers of amino acid derivatives such as for example, amino hexanoic acids, and combinations thereof. Diamines are molecules of the general formula $NH_2RNH_2$, where R is a branched or unbranched hydrocarbon (a molecule composed of carbon and hydrogen) having from 2 to 25 carbon atoms, wherein one or more carbon atoms may be replaced by oxygen, sulfur, silicon, and or nitrogen atoms. Examples of diamines include ethylene diamine and diamino propane. Diacids are molecules of the general formula R'OOC—R"—COOR', where R" is a branched or unbranched hydrocarbon having from 2 to 25 carbon atoms, wherein one or more carbon atoms may be replaced by oxygen, sulfur, silicon, and or nitrogen atoms, and R' is H or a hydrocarbon having from 1 to 10 carbon atoms. Typically, the OR' groups are removed during the reactions to attach the spacer molecule to the substrate surface and attach the spacer molecule to the nascent polymer and the resulting linker molecule has the structure —CO—R"—CO—. Alternatively, the spacers may be the same molecule type as that being synthesized (i.e., nascent polymers), such as polynucleotides, oligonucleotides and peptides.

Electrode arrays are optionally used both to perform solid-phase synthesis of nucleic acids and peptides on the surface of the electrode and to detect the presence of single and double stranded nucleic acids or peptide molecular recognition reactions on the surface of the electrode. For an electrode functionalized with a probe nucleic acid molecule exposed to a solution containing a target nucleic acid molecule, the presence of double stranded nucleic acids on the surface of the electrode is indicative of the occurrence of a hybridization reaction. Electronic detection provides the ability to monitor synthesis and hybridization reactions in real time without the use of labels. Since no wash is required to remove unbound labeled analytes, binding kinetics can be monitored using dynamic measurements at the solid-solution interface.

Electronic detection is the detection of a molecule through a measurement of voltage, resistance, and or current characteristics of an electronic sensor in the presence of the molecules to be detected. Optionally, the electronic signal measured in the presence of the molecule to be detected is compared to an electronic signal measured in the absence of the molecules to be detected.

A wafer refers to a semiconductor substrate used in the fabrication of integrated circuits and other microdevices and is for example a substrate comprised of a silicon crystal. The wafer serves as a substrate for a microelectronic device having a large number of electronic features that is built through the use of nano and microfabrication techniques such as deposition of various materials, such as conductors, semiconductors, and insulators, photolithographic patterning, etching, and ion implantation.

Optionally, an integrating charge amplifier is connected to an electrode (or the electrodes comprising the array) and configured to detect capacitance changes at the electrode surface. A differential amplifier (or a differential-input single-ended output amplifier) is a device that amplifies the difference between two input signals (−) and (+). Optionally, the integrating charge amplifier includes a drive circuit that is capable of providing voltage pulses which can be supplied, for example, as a square, sine, or sawtooth wave form to a solution-accessible (exposed) electrode. The integrating charge amplifier optionally also includes an input that is from an exposed sensing electrode and another input from a solution-exposed or unexposed reference electrode.

A device including one or more integrating charge amplifiers is preferably configured to measure the integrated charge and effective capacitance at the analyte-electrode interface. A change in integrated charge or effective capacitance can then be used to ascertain whether a hybridization or other molecular recognition reaction has occurred (i.e., whether analytes have bound at the electrode surface or to the affinity probe attached to the electrode surface). An array of integrating amplifiers and a corresponding electrode array are optionally fabricated on the same substrate. The substrate may also include synthesis and detection drive circuits, logic for switching, latches, memory, input/output devices.

Figure 9:
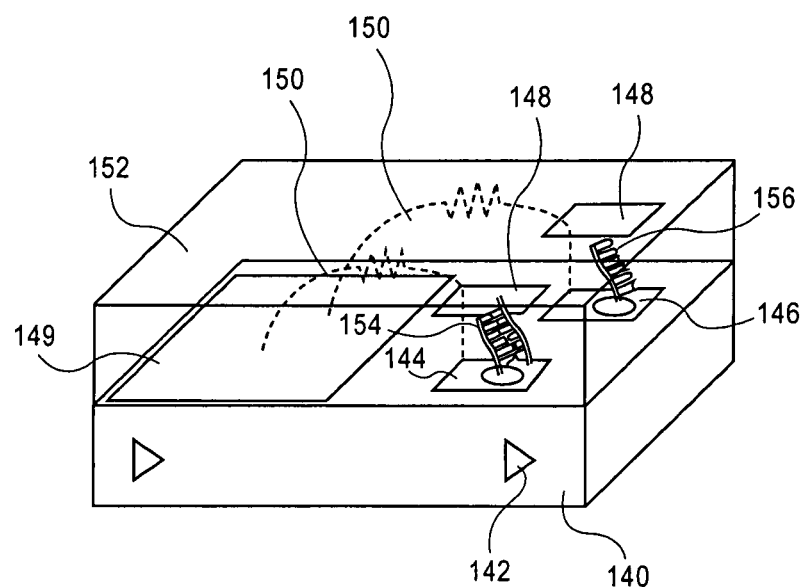
FIG. 9 provides a schematic of the electronic detection of a molecular recognition event using an array of exposed electrodes.

FIG. 9 provides a schematic of an exemplary electronic device capable of detecting a hybridization event between a surface-attached DNA probe molecule and a target molecule. The electronic molecular detection device has a substrate 140 that houses electronics for detecting 142 (as described more fully herein), exposed sensing electrodes 144, exposed reference electrode 146, and drive electrode 149. The electrodes 144, 146, and 149 are connected to electronics through physical electrical connections. In FIG. 9, dotted lines 150 demonstrate resistive and capacitive paths (virtual capacitive plates 148 are shown) established in the conductive matrix of buffer solution 152 and insulating affinity probe/analyte layer 154 on the electrode 144. The probe/analyte layer 154 is not to scale with respect to the electrode size and only one probe/analyte complex is shown (for simplicity) where many would typically be attached to an electrode surface. In FIG. 9, the electronic detection device can be operated in differential detection mode, in which both reference electrodes 146 and sensing electrodes 144 have attached affinity probes 154 and 156. The electronics 142 comprising a differential charge amplifier provide differential sensing data to an output amplifier and A/D or analog output.

For measurements of effective capacitance, the analyte is preferably provided in a conductive solution that provides a conductive path between the driving and the integrating electrodes of the amplifier. A conductive solution comprises for example, an aqueous solution having an ionic concentration or a conductive gel. A preferred method for operating a device including one or more integrating charge amplifiers includes providing a voltage pulse through the drive electrode to the conductive matrix. This pulse can be applied to the matrix with respect to an integrating electrode and the charge is accumulated on the integrating electrode over a fixed time.

Figure 10:
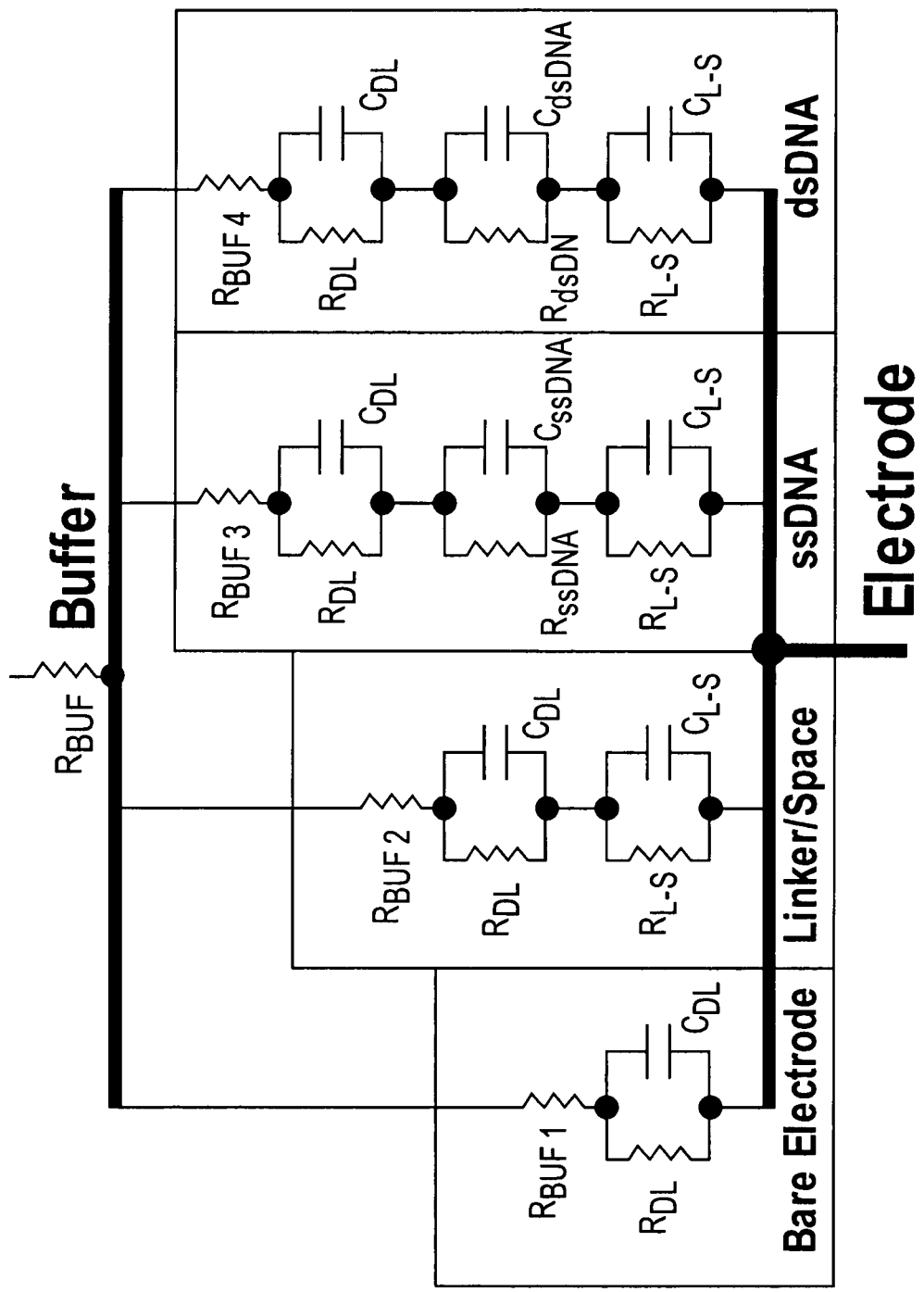
FIG. 10 shows a circuit model for the electronic detection of a molecular recognition event on an electrode.

The measured capacitance is established by the fixed sensing electrode, the dielectric formed by the attachment chemistry, attached probe, and bound analyte (if present), and a virtual parallel plate formed above the sense electrodes by the charge/ion distribution in the matrix. The measured capacitance is a function of the electrode area, the dielectric constant, and the distance of the virtual plate from the sensing electrode. Analytes binding to the electrode or the attached affinity probe will change the dielectric constant and or the distance between the virtual plate and the sensing electrode, thereby changing the effective capacitance and accumulated charge on the sensing electrode when a voltage is applied. The area and distance to the drive electrode are not material since the conductive matrix carries the voltage to the virtual plate. FIG. 10 provides a theoretical circuit model for the electronic detection of a hybridization reaction. In FIG. 10, ssDNA (single stranded DNA) represents the probe attached to the electrode and dsDNA (double stranded DNA) represents the probe hybridized to a target analyte. Any capacitance contributed by the drive electrode is in series with the measured capacitance and is small owing to the large electrode area.

The solution-accessible (or exposed) electrodes used in embodiments of the invention are made from metals, combinations of metals, or other conducting materials. For example, an electrode may be made from, for example, platinum, palladium, nickel, copper, iridium, aluminum, titanium, tungsten, gold, rhodium, as well as alloys of metals, conducting forms of carbon, such as glassy carbon, reticulated vitreous carbon, basal plane graphite, edge plane graphite, graphite, indium tin oxide, conducting polymers, metal doped conducting polymers, conducting ceramics, and conducting clays. A functionalized electrode is an electrode having a probe molecule that has a specific affinity for a target molecule attached to the electrode surface. An unfunctionalized electrode is an electrode having no probe molecule attached or an attached molecule that has no specific chemical affinity for a target molecule to be analyzed. In one embodiment the electrode is comprised of platinum. In a further embodiment the electrode is comprised of palladium.

Electrodes are connected to sensing and driving circuitry according to known methods. For example, CMOS (complementary metal oxide semiconductor) circuitry could be used, magnetic radiation-addressable switches, direct connections from an electrode to a bond pad on the perimeter of a semiconductor chip, and or combinations thereof. Data is optionally gathered and analyzed using a computer.

Electrodes are connected to a source capable of providing voltage and current. For example, electrodes that form an array are connected to CMOS (complementary metal oxide semiconductor) switching circuitry, radio frequency (RF) and microwave addressable devices, light addressable devices, and or metal lines leading to the perimeter of the array. In embodiments of the invention, CMOS switching circuitry involves the connection of each of the electrodes to a CMOS transistor switch and provides the ability to individually address electrodes comprising an array. The switch is accessed by sending an electronic address signal down a common bus to SRAM (static random access memory) circuitry associated with the electrode. Radio and microwave frequency addressable switches involve the switching between on and off states through the use of a microwave or RF radiation. RF and microwave frequency switches can be tuned to receive a particular frequency or modulation frequency and switch without the use of array-based switching logic. Light addressable switches are moved between on and off positions by light in the ultraviolet through infra red frequency ranges. An electromagnetic signal can be spatially localized to provide switching.

EXAMPLES

In general, the production of a DNA array is as follows: An array chip was placed in the chamber of a DNA synthesizer programmed to run standard cyanoethyl phosphoramidite DNA synthesis. The acid deblocking reagent was replaced with an electrochemical deblocking mixture. The electrochemical deblocking mixture was hydroquinone (22 g), anthraquinone (2.0 g), tetraethylammonium p-toluene sulfonate (60 g) in a mixture of 400 mL methanol and 2.5 L acetonitrile. The mixture was stirred thoroughly, and 2,6-lutidine was added (2.32 mL), and the volume was brought to a total of 4.0 L with added acetonitrile and stirred until fully dissolved. The synthesis chamber allows the chip's electrode surface to be exposed to various solutions and allows electrical connection between the chip and a computer to determine which electrodes will be used at each stage of synthesis process. The counter electrode was a sheet of platinum on the opposing wall of the synthesis chamber. Once the synthesis was finished, the chip was removed from the chamber, deprotected chemically to remove terminal DMT protecting groups, and then exposed to ethylenediamine in ethanol (1:1 v/v) for 1 hour at 65° C. to remove side chain protective groups and cyanoethyl protecting groups.

The invention claimed is:

1. A method for synthesizing nucleic acids on a surface comprising,
   providing a substrate comprised of at least one drive electrode, at least one sensing electrode, and at least one reference electrode, wherein the at least one drive electrode is connected to both drive circuitry configured to drive polymer synthesis and an integrating charge amplifier, wherein the electrodes have a surface, and wherein a surface area of a drive electrode is larger than a surface area of a reference electrode;
   attaching a cleavable linker to the surface of at least one reference, drive, or sensing electrode, and
   electrochemically synthesizing a nucleic acid polymer that is attached to the cleavable linker wherein electrochemically synthesizing comprises electrochemically generating an acid by passing current through an electrode, removing a protecting group from an end of a polymer growth site, and coupling a nucleic acid monomer to the polymer growth site wherein the nucleic acid monomer has a protecting group that prevents further polymer growth after the nucleic acid monomer is coupled to the polymer growth site, and wherein generating, removing, and coupling occur a plurality of times.

2. The method of claim 1 additionally comprising passing current through a reference, drive, or sensing electrode to cause the cleavage of the cleavable linker and release an electrochemically synthesized nucleic acid polymer.

3. The method of claim 1 wherein the at least one reference, drive, or sensing electrode is comprised of platinum and the cleavable linker is coupled to the surface through a silane molecule.

4. The method of claim 1 wherein a feature size of the array is less than 100 µm$^2$.

5. The method of claim 1 wherein the at least one reference, drive, or sensing electrode is comprised of platinum, palladium, nickel, copper, iridium, aluminum, titanium, tungsten, gold, rhodium, glassy carbon, conducting graphite, and combinations thereof.

6. The method of claim 1 wherein a nucleic acid monomer additionally comprises a label.

7. The method of claim 6 wherein the label comprises a molecule that is detectable through UV-vis spectroscopy or fluorescence spectroscopy.

8. The method of claim 1 wherein the cleavable linker is attached to the surface of the at least one reference, drive, or sensing electrode through a linker molecule.

9. The method of claim 1 wherein the cleavable linker is cleavable through the oxidation or reduction of the cleavable linker.

10. The method of claim 1 wherein the cleavable linker is cleavable through the action of an electrogenerated acid or an electrogenerated base.

11. A method for synthesizing peptides on a surface comprising,
providing a substrate comprised of at least one drive electrode, at least one sensing electrode, and at least one reference electrode, wherein the at least one drive electrode is connected to both drive circuitry configured to drive polymer synthesis and an integrating charge amplifier, wherein the electrodes have a surface, and wherein a surface area of a drive electrode is larger than a surface area of a reference electrode;
attaching a cleavable linker to the surface of at least one reference, drive, or sensing electrode, and
electrochemically synthesizing a peptide polymer coupled to the cleavable linker wherein electrochemically synthesizing comprises electrochemically generating an acid by passing current through an electrode, removing a protecting group from an end of a polymer growth site, and coupling an amino acid wherein the amino acid has a protecting group that prevents further polymer growth after the amino acid is coupled to the polymer growth site, and wherein generating, removing, and coupling occur a plurality of times.

12. The method of claim 11 additionally comprising passing current through a reference, drive, or sensing electrode to cause the cleavage of the cleavable linker and release an electrochemically synthesized peptide polymer.

13. The method of claim 11 wherein the at least one reference, drive, or sensing electrode is comprised of platinum and the cleavable linker is coupled to the surface through a silane molecule.

14. The method of claim 11 wherein a feature size of the array is less than 100 µm$^2$.

15. The method of claim 11 wherein the at least one reference, drive, or sensing electrode is comprised of platinum, palladium, nickel, copper, iridium, aluminum, titanium, tungsten, gold, rhodium, glassy carbon, conducting graphite, and combinations thereof.

16. The method of claim 11 wherein an amino acid additionally comprises a label.

17. The method of claim 16 wherein the label comprises a molecule that is detectable through UV-vis spectroscopy or fluorescence spectroscopy.

18. The method of claim 11 wherein the cleavable linker is attached to the surface of the reference, drive, or sensing electrode through a linker molecule.

19. The method of claim 11 wherein the cleavable linker is cleavable through the oxidation or reduction of the cleavable linker.

20. The method of claim 11 wherein the cleavable linker is cleavable through the action of an electrogenerated acid or an electrogenerated base.

21. An electronic array comprising,
a substrate having at least one drive electrode, at least one sensing electrode, and at least one reference electrode, wherein the at least one drive electrode is connected to both drive circuitry configured to drive nucleic acid or peptide polymer synthesis and an integrating charge amplifier, wherein the electrodes comprise a surface, wherein a surface area of a drive electrode is larger than a surface area of a reference electrode, and wherein the surface of at least one reference, drive, or sensing electrode comprises a cleavable linker attached to the surface of the electrode.

22. The electronic array of claim 21 wherein the cleavable linker is attached to the surface through a silane linker molecule.

23. The electronic array of claim 21 wherein the electrodes are comprised of platinum.

24. The electronic array of claim 21 wherein the cleavable linker is attached to the surface through a silane linker molecule and the electrodes are comprised of platinum.

25. The electronic array of claim 21 wherein a feature size of the array is less than 100 µm$^2$.

26. The electronic array of claim 21 wherein the cleavable linker is cleavable through the oxidation or reduction of the cleavable linker.

27. The electronic array of claim 21 wherein the cleavable linker is cleavable through the action of an electrogenerated acid or an electrogenerated base.

28. The electronic array of claim 21 wherein the at least one reference, drive, or sensing electrode comprising a cleavable linker is comprised of platinum, palladium, nickel, copper, iridium, aluminum, titanium, tungsten, gold, rhodium, glassy carbon, conducting graphite, or combinations thereof.

29. The electronic array of claim 21 wherein the cleavable linker is cleavable through the oxidation or reduction of the cleavable linker.

* * * * *